United States Patent
Winston

[19]

[11] Patent Number: 5,916,210
[45] Date of Patent: Jun. 29, 1999

[54] CATHETER FOR LASER TREATMENT OF ATHEROSCLEROTIC PLAQUE AND OTHER TISSUE ABNORMALITIES

[75] Inventor: Thomas R. Winston, Leawood, Kans.

[73] Assignee: IntraLuminal Therapeutics, Inc., Carlsbad, Calif.

[21] Appl. No.: 08/851,409

[22] Filed: May 5, 1997

Related U.S. Application Data

[63] Continuation of application No. 08/249,378, May 24, 1994, abandoned, which is a continuation of application No. 08/101,343, Aug. 2, 1993, abandoned, which is a continuation of application No. 07/672,822, Mar. 21, 1991, abandoned, which is a continuation-in-part of application No. 07/470,722, Jan. 26, 1990, abandoned.

[51] Int. Cl.$^6$ .................................................. A61N 5/06
[52] U.S. Cl. ..................... 606/7; 606/10; 606/15; 606/17; 606/18; 600/439; 600/443; 600/7
[58] Field of Search .................. 606/1–19; 600/437–447

[56] References Cited

U.S. PATENT DOCUMENTS

| | | |
|---|---|---|
| 3,264,863 | 8/1966 | Maropis . |
| 3,470,868 | 10/1969 | Krause et al. ..................... 128/660.09 |
| 3,779,234 | 12/1973 | Eggleton et al. . |
| 3,915,018 | 10/1975 | Karplus . |
| 3,938,502 | 2/1976 | Bom . |
| 4,008,455 | 2/1977 | Pederson . |
| 4,208,917 | 6/1980 | Aoyama et al. . |
| 4,284,473 | 8/1981 | Kasama . |
| 4,337,661 | 7/1982 | Kretz ................................. 128/660.09 |
| 4,349,032 | 9/1982 | Koyata ............................... 128/662.06 |
| 4,462,408 | 7/1984 | Silverstein et al. . |
| 4,466,443 | 8/1984 | Utsugi ................................. 128/660.1 |
| 4,576,177 | 3/1986 | Webster, Jr. . |
| 4,587,972 | 5/1986 | Morantte . |
| 4,605,009 | 8/1986 | Pourcelot et al. . |
| 4,685,450 | 8/1987 | Collins et al. .............................. 128/6 |
| 4,757,818 | 7/1988 | Angelsen . |
| 4,764,334 | 8/1988 | King et al. . |
| 4,794,931 | 1/1989 | Yock . |
| 4,869,258 | 9/1989 | Hetz .................................... 128/662.06 |
| 4,887,605 | 12/1989 | Angelsen et al. . |
| 4,930,515 | 6/1990 | Terwilliger . |
| 4,950,267 | 8/1990 | Ishihara et al. . |
| 4,951,677 | 8/1990 | Crowley et al. . |
| 4,957,112 | 9/1990 | Yokoi et al. . |
| 4,972,839 | 11/1990 | Angelsen . |
| 5,054,492 | 10/1991 | Scribner et al. . |

(List continued on next page.)

FOREIGN PATENT DOCUMENTS

| | | |
|---|---|---|
| 65275 | 11/1982 | European Pat. Off. ................... 128/6 |
| A0325836 | 8/1989 | European Pat. Off. . |
| A0329492 | 8/1989 | European Pat. Off. . |
| 0127665 | 6/1987 | Japan . |
| 62-270140 | 11/1987 | Japan . |
| 376712 | 4/1973 | U.S.S.R. . |
| WO8701269 | 3/1987 | WIPO . |

OTHER PUBLICATIONS

"Similarities and Differences Between Fiber Acoustics and Fiber Optics" C.K. Jen, Dated 1985.

*Primary Examiner*—David M. Shay
*Attorney, Agent, or Firm*—Armstrong, Teasdale, Schlafly & Davis

[57] ABSTRACT

A medical catheter for treating atherosclerotic plaque and other abnormalities includes optical fibers for applying laser energy to the plaque and an ultrasonic transducer system for sensing the location and configuration of the plaque. The optical fibers and electrical wiring for the transducers extend through a probe which is rotatable inside of the catheter tube to provide universal directional control of the fibers and transducers. A reflective system includes a curved reflector in the probe which can be axially adjusted to vary the directions of the ultrasonic signals. Alternative forms of the invention include different reflector schemes, an angled ultrasonic transducer having a conical signal output that varies with frequency, and various different systems for rotating the transducers and fibers.

18 Claims, 5 Drawing Sheets

U.S. PATENT DOCUMENTS

| | | |
|---|---|---|
| 5,152,291 | 10/1992 | Dias . |
| 5,163,432 | 11/1992 | Ueno et al. . |
| 5,170,793 | 12/1992 | Takano et al. . |
| 5,195,519 | 3/1993 | Angelsen . |
| 5,217,018 | 6/1993 | Dias . |
| 5,254,112 | 10/1993 | Sinofsky et al. . |
| 5,257,628 | 11/1993 | Ishiguro et al. . |
| 5,284,148 | 2/1994 | Dias et al. . |

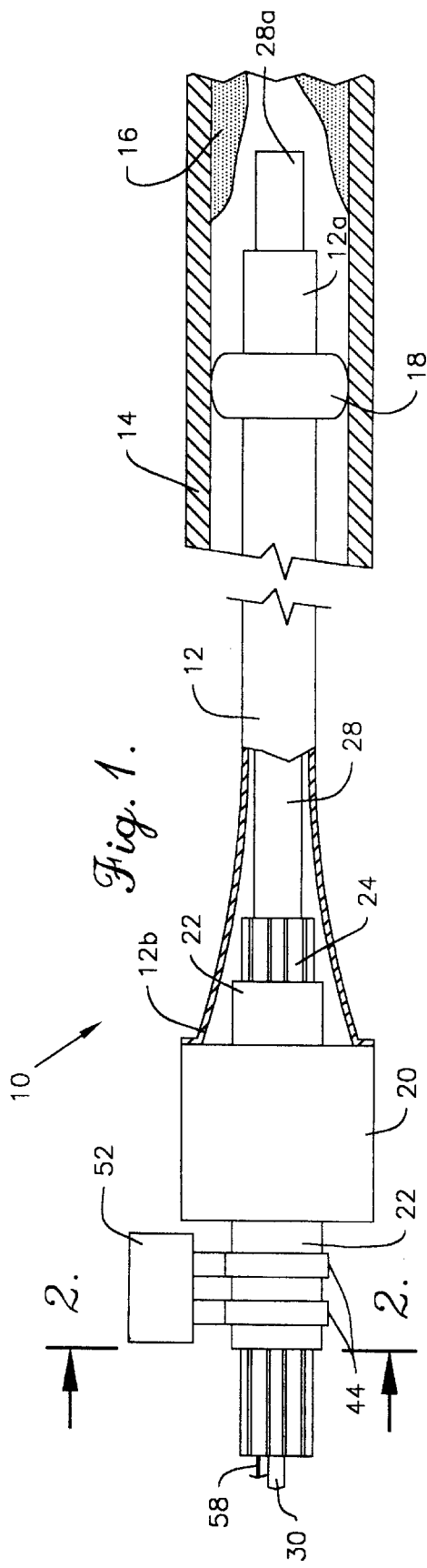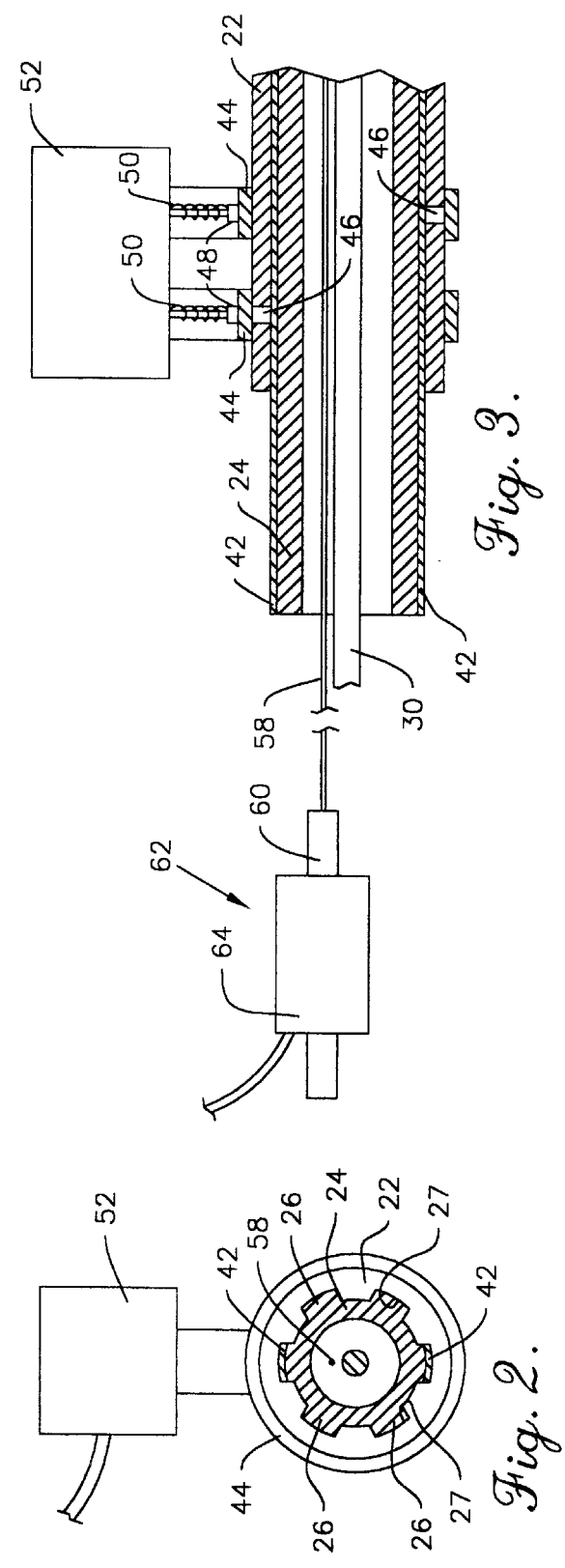

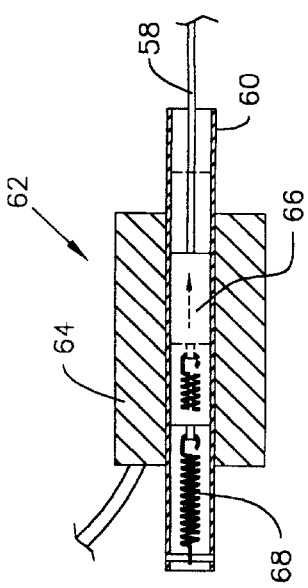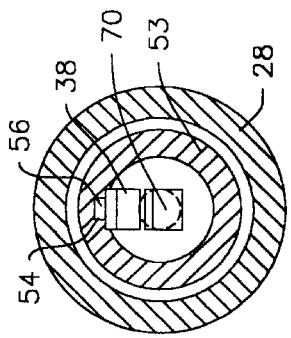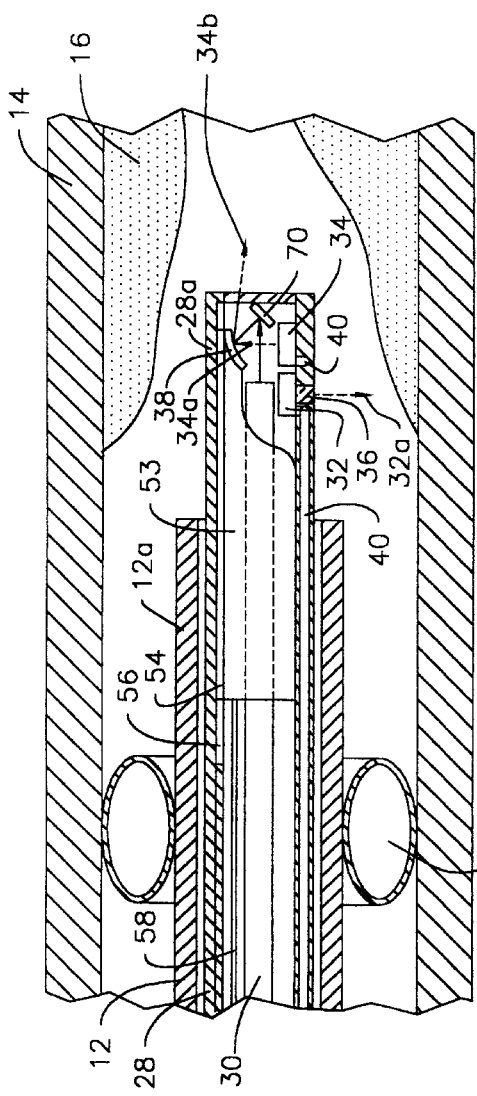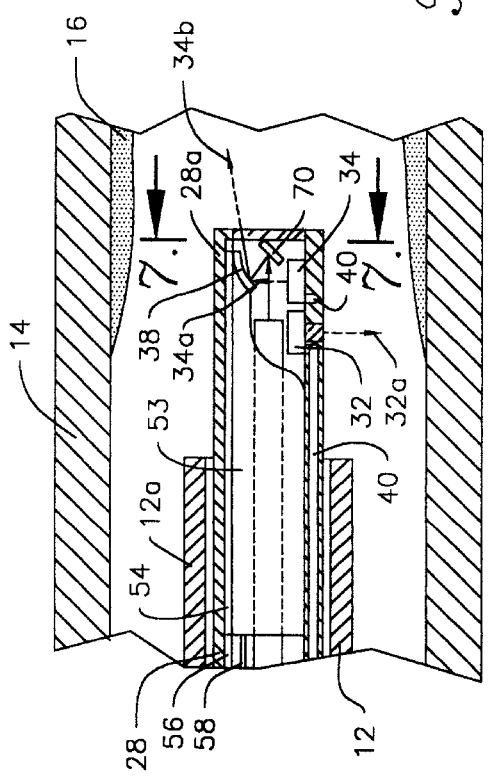

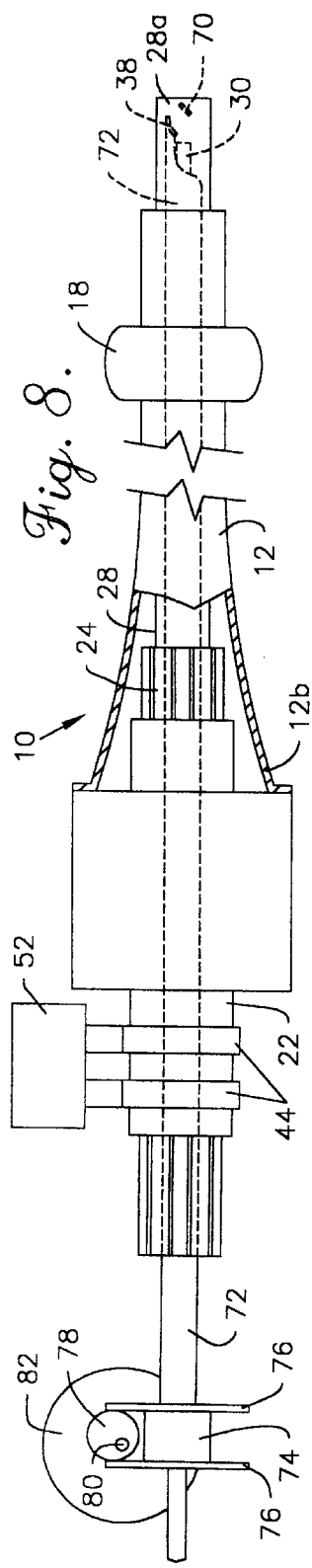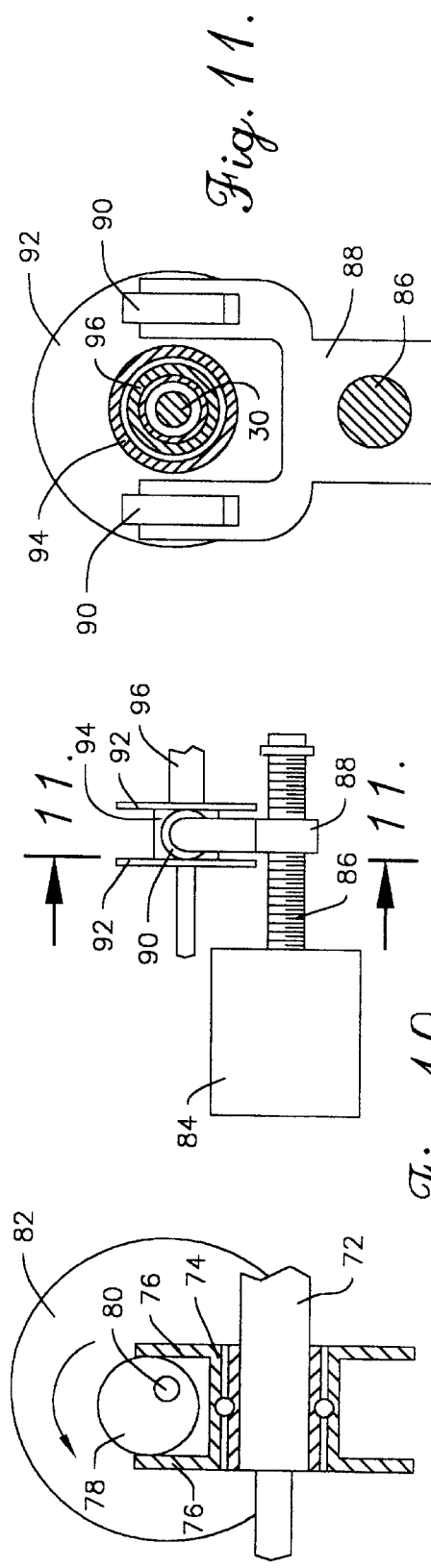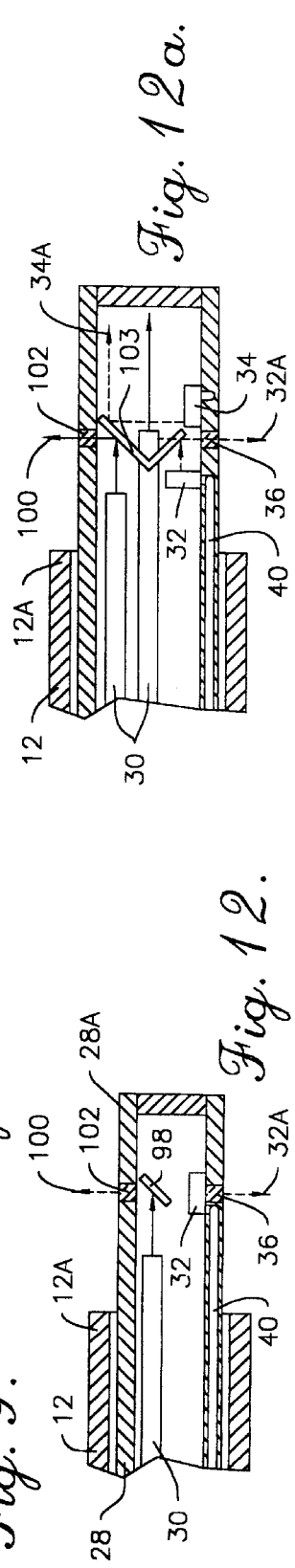

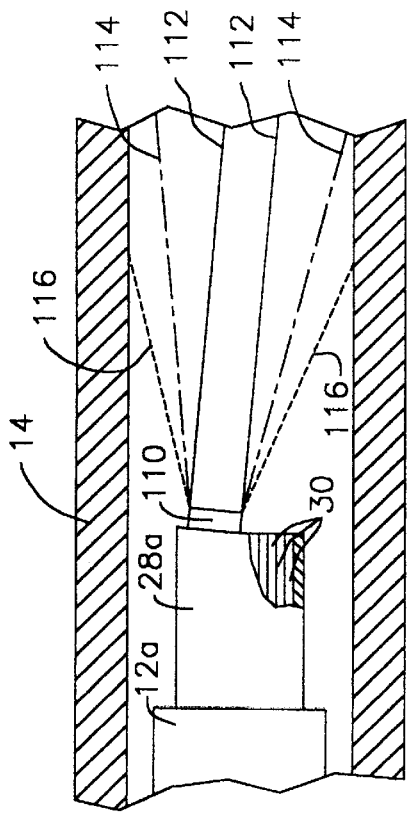
Fig. 13.
Fig. 14.
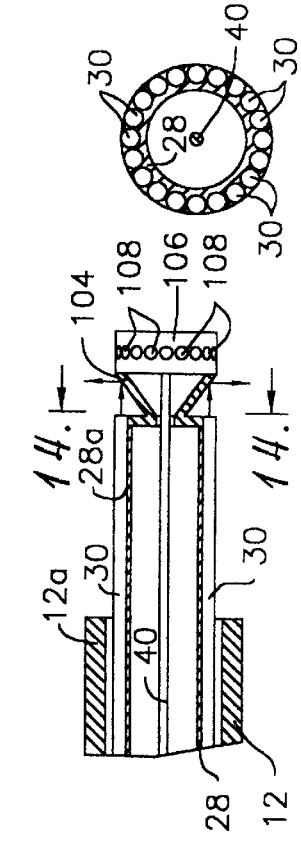
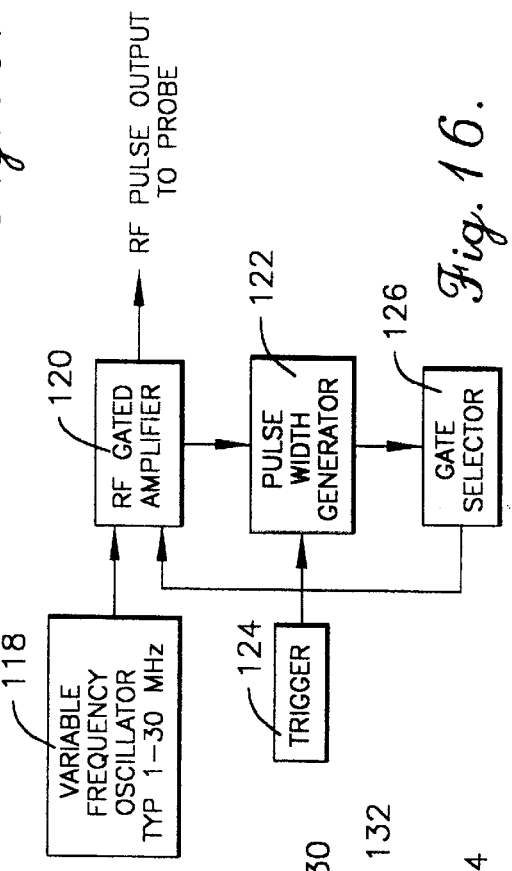
Fig. 15.
Fig. 16.
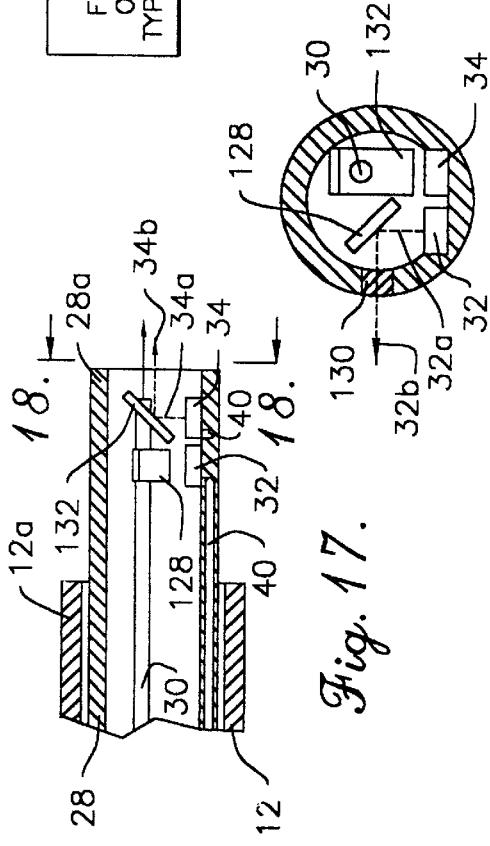
Fig. 17.
Fig. 18.

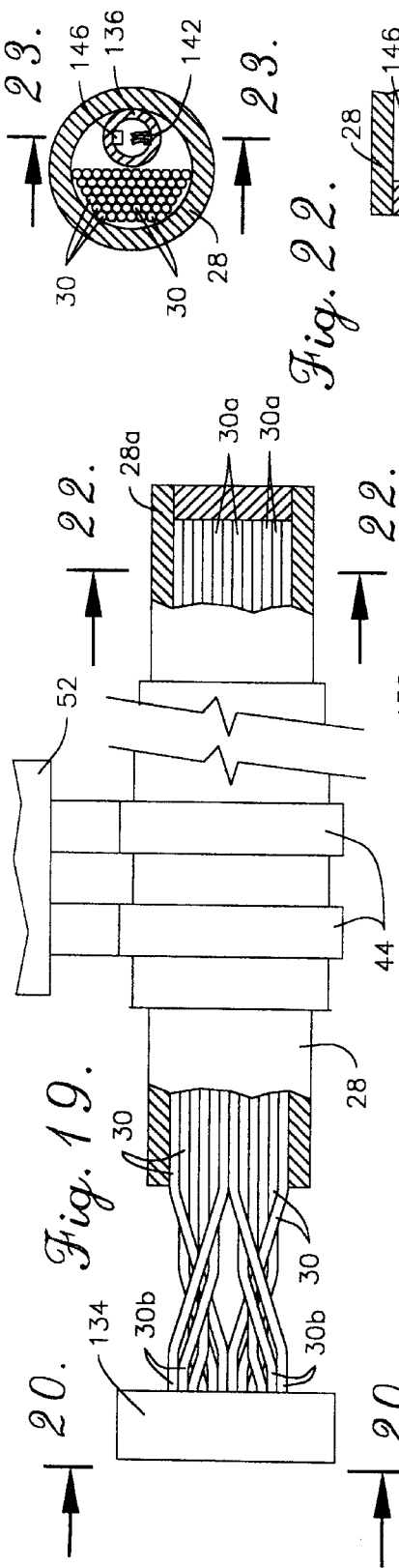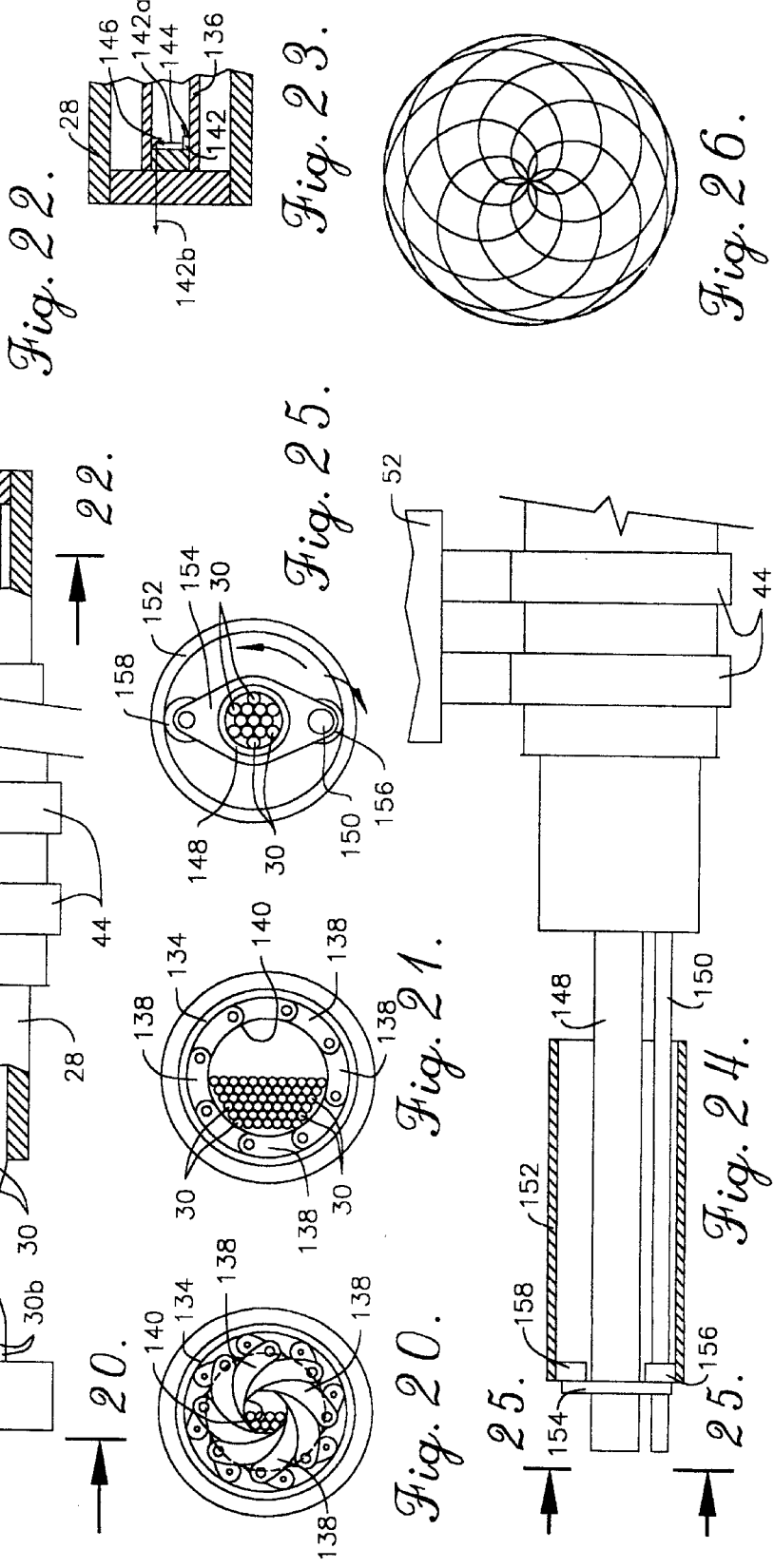

CATHETER FOR LASER TREATMENT OF ATHEROSCLEROTIC PLAQUE AND OTHER TISSUE ABNORMALITIES

RELATED APPLICATION

This application is a continuation of application Ser. No. 08/249,378, filed May 24, 1994, now abandoned, which is a continuation of application Ser. No. 08/101,343 filed Aug. 2, 1993 now abandoned, which is a continuation of application Ser. No. 07/672,822 filed Mar. 21, 1991 now abandoned, which is a continuation in part of patent application Ser. No. 470,722, filed on Jan. 26, 1990 in the name of Thomas R. Winston for "APPARATUS FOR PHOTOBLATIVE TREATMENT OF ATHEROSCLEROTIC LESIONS".

FIELD OF THE INVENTION

This invention relates generally to the medical use of laser energy and deals more particularly with a catheter which is equipped with optical fibers for the transmission of laser energy and also with an ultrasonic transducer system for sensing the character and configuration of the area that is to be medically treated by the laser energy.

BACKGROUND OF THE INVENTION

It has long been known that cardiovascular problems are caused by the presence of atherosclerotic plaque on the walls of veins and arteries, especially coronary arteries. For some time, there has been interest in the use of laser energy to remove plaque and to treat abnormalities on internal organs in the body. Typically, it is proposed to use a catheter that contains optical fibers for transmitting the laser energy through the catheter to the area that is to undergo treatment. Lasers have also been used to treat other medical problems such as tumors or other abnormalities in the colon, esophagus, prostrate and other areas of the body.

U.S. Pat. No. 4,576,177 to Webster discloses a catheter which includes optical fibers in combination with an ultrasonic transducer having the capability of transmitting and receiving ultrasonic signals. The reflections of the ultrasonic signals from the tissue are received by the transducer to provide information as to the character and configuration of the tissues so that the laser energy can be applied properly to the plaque lesion and not to unoccluded artery walls or other healthy tissues.

In the device disclosed in the Webster patent, the ultrasonic transducer takes the form of a flat ring which is oriented at an angle to the axis of the catheter. With this arrangement, it is necessary to rotate the catheter through a full 360° circle in order to direct the ultrasound at the entire circumference of the artery. The need to manually rotate the catheter is at best a severe inconvenience and an inaccurate procedure because the catheter cannot be accurately stepped through incremental arcs in order to provide a reliable profile of the arterial plaque. If the ultrasound techniques are inadequate to provide the instrument with an accurate configuration of the plaque, the laser energy can be misdirected such that it is not only ineffective in treating the problem but also possibly destructive of healthy tissues.

SUMMARY OF THE INVENTION

The present invention is an improvement over the catheter described in the previously mentioned Webster patent and is directed primarily at providing an ultrasonic system that is improved in its accuracy, practicality and reliability.

In accordance with the invention, a catheter equipped with an optical fiber for transmitting laser energy is also provided with an ultrasonic sensing system that is able to accurately determine the character and configuration of the entirety of an artery wall or other treatment area without the need for manual turning of the catheter. In one form of the invention, the ultrasound system is carried by a probe that extends through the catheter and may be rotated inside of the catheter by a stepping motor or the like in order to sweep the ultrasonic sensing system through 360° in selected increments. As a result, accurate information can be obtained as to the profile of an occlusion or other abnormality. One ultrasonic transducer can be oriented radially to sweep around the entire circumference of the artery as the probe is rotated. In many cases, it is desirable to provide a second ultrasonic transducer which is oriented to direct ultrasonic signals forwardly, either parallel to the catheter axis or at a slight angle to it to sense the artery geometry ahead of the probe.

The invention is particularly characterized in one of its forms by a concave reflector which directs the ultrasonic signal forwardly from the second transducer. The reflector can be axially adjusted in order to vary the angle of the reflected signal relative to the catheter axis. This permits the tissue profile ahead of the probe to be determined accurately and at different locations along the artery. The adjustment of the reflector can be carried out in a variety of different ways, and the probe itself can be adjusted axially for even more versatility of the instrument.

In another form of the invention, the probe is stationary relative to the catheter but is equipped with a number of optical fibers which are arranged in a circular pattern around the circumference of the probe. A conical mirror on the tip of the probe directs the laser energy from each fiber in a radial direction so that all areas around the circumference of the probe can be treated without need for rotation of the catheter or probe. A phased array of ultrasonic transducers transmits radial ultrasonic signals and permits the configuration of the artery wall around its entire circumference to be sensed without rotation of the catheter or probe.

Still another form of the invention includes a probe through which the optical fibers extend and a smaller tube located within the probe and housing an ultrasonic transducer. The probe is rotatable within the catheter, and the smaller tube is itself rotatable within the probe. The optical fibers are arranged so that those having their inner ends closest to the center of the catheter have their outer ends farthest from the center. Consequently, when a shutter which controls the application of laser energy to the fibers is progressively closed, the fibers whose inner ends are closest to the center are deenergized first and the areas nearest the artery walls are treated last.

Other and further objects of the invention, together with the features of novelty appurtenant thereto, will appear in the course of the following description.

DESCRIPTION OF THE DRAWINGS

In the accompanying drawings which form a part of the specification and are to be read in conjunction therewith and in which like reference numerals are used to indicate like parts in the various views:

FIG. 1 is a fragmentary side elevational view of a catheter constructed according to one embodiment of the present invention, with portions shown in section for illustrative purposes and the break lines indicating continuous length;

FIG. 2 is a fragmentary sectional view on an enlarged scale taken generally along line 2—2 of FIG. 1 in the direction of the arrows;

FIG. 3 is a fragmentary sectional view of the outer end portion of the probe for the catheter, showing a control wire and actuator for adjusting a mirror included in the tip end of the probe;

FIG. 4 is a fragmentary sectional view on an enlarged scale of the tip ends of the probe and catheter;

FIG. 5 is a fragmentary sectional view similar to FIG. 4, but showing the mirror adjusted toward the tip of the probe from the position shown in FIG. 4;

FIG. 6 is a fragmentary sectional view showing the actuator for the control wire of the mirror;

FIG. 7 is a fragmentary sectional view on an enlarged scale taken generally along line 7—7 of FIG. 5 in the direction of the arrows;

FIG. 8 is a fragmentary side elevational view showing a catheter equipped with a cam drive system for adjusting the mirror in accordance with an alternative embodiment of the invention;

FIG. 9 is a fragmentary sectional view on an enlarged scale showing the cam drive system for the mirror;

FIG. 10 is a fragmentary side elevational view showing a drive system for axial adjustment of the probe within the catheter;

FIG. 11 is a fragmentary sectional view taken generally along line 11—11 of FIG. 10 in the direction of the arrows;

FIG. 12 is a fragmentary sectional view of the tip end of a catheter and probe constructed according to an alternative embodiment of the invention;

FIG. 12a is a fragmentary sectional view of the tip end of a catheter and probe constructed according to another alternative embodiment of the invention;

FIG. 13 is a fragmentary sectional view of the tip end of yet another alternative catheter and probe constructed according to the invention;

FIG. 14 is a fragmentary sectional view on an enlarged scale taken generally along line 14—14 of FIG. 13 in the direction of the arrows;

FIG. 15 is a fragmentary elevational view, partially in section, showing the tip end of yet another alternative catheter constructed according to the invention;

FIG. 16 is a block diagram of the electronic system used to excite the ultrasonic transducer of the catheter;

FIG. 17 is a fragmentary sectional view of the tip end of still another alternative catheter constructed according to the invention;

FIG. 18 is a fragmentary end elevational view on an enlarged scale taken generally along line 18—18 of FIG. 17 in the direction of the arrows;

FIG. 19 is a fragmentary side elevational view, partially in section, showing still another alternative catheter constructed according to the invention;

FIG. 20 is a fragmentary end elevational view taken generally along line 20—20 of FIG. 19 in the direction of the arrows, with the shutter which controls the application of laser energy to the optical fibers partially closed;

FIG. 21 is an end elevational view similar to FIG. 20, but showing the shutter in the fully open position;

FIG. 22 is a fragmentary sectional view taken generally along line 22—22 of FIG. 19 in the direction of the arrows;

FIG. 23 is a fragmentary sectional view taken generally along line 23—23 of FIG. 22 in the direction of the arrows;

FIG. 24 is a fragmentary elevational view of yet another alternative catheter constructed according to the invention;

FIG. 25 is a fragmentary end elevational view on an enlarged scale taken generally along line 25—25 of FIG. 24 in the direction of the arrows; and FIG. 26 is a diagrammatic view of the path traced by the ultrasonic transducer shown in FIG. 22 as the probe and transducer tube are rotated.

DETAILED DESCRIPTION OF THE INVENTION

Referring now to the drawings in more detail and initially to FIG. 1, numeral 10 generally designates a catheter which is constructed according to a first embodiment of the present invention. The catheter 10 includes a hollow catheter tube 12 having an elongated configuration and a circular cross section. The catheter tube 12 has a size and construction to be inserted into the body to the area which is to undergo treatment. For example, if the catheter tube 12 is to be used for the treatment of atherosclerotic plaque, it should be small enough to be inserted into an artery such as the artery 14 which is plagued by the presence of plaque 16 on the interior of the artery wall. An annular balloon seal 18 may be provided on the inner end 12a of the catheter tube in order to provide a seal against the artery wall.

The opposite or outer end of the catheter tube 12 is designated by numeral 12b in FIG. 1 and may be secured to a stationary motor 20 which is preferably an electrical stepping motor. Referring additionally to FIG. 2, the motor 20 rotates an output shaft 22. A lined sleeve 24 fits within the output shaft 22 of the motor and is provided with a plurality of splines 26 that interfit with internal key ways 27 on the shaft 22. Consequently, the sleeve 24 is rotated directly with the shaft 22 but is able to slide axially relative to shaft 22 by reason of the sliding movement that is permitted of the splines 26 within the key ways 27 which receive them.

Sleeve 24 is fitted on and rigidly fixed to an elongated tubular probe 28 which extends through the length of the catheter tube 12 and is coaxial with it. The probe 28 is smaller in diameter than the catheter tube 12 and has an outer end to which sleeve 24 is fixed and an inner end 28a which projects out of the inner end 12a of the catheter tube. An optical fiber 30 extends through substantially the entire length of the probe 28, with the free end of the fiber 30 terminating within the inner end 28a of the probe. The optical fiber 30 extends substantially along the longitudinal axis of the probe and catheter tube and receives and transmits energy from a conventional medical laser (not shown).

Referring additionally to FIGS. 4–7, the tip end 28a of probe 28 is provided with a pair of conventional ultrasonic transducers 32 and 34 which are mounted inside of the probe 28. the transducers 32 and 34 may be excited electrically in order to transmit ultrasonic signals, and the transducers also receive pulse echoes which are reflections of the transmitted signals. The received pulse echoes are transformed by the transducers into electrical signals to provide information as to the configuration and character of the tissues from which the signals are reflected. The transducers are preferably piezoelectric ceramic crystals.

The first transducer 32 is oriented to transmit a signal 32a (See FIG. 4) which is directed radially outwardly of the catheter and probe through a window 36 in the wall of the probe 28. The second transducer 34 is oriented to transmit an ultrasonic signal 34a radially inwardly toward a concave reflector 38 from which the signal 34a reflects generally forwardly from the tip end of the probe 28, as indicated at 34b in FIGS. 4 and 5.

Electrical conductors 40 extend through the probe 28 and connect electrically with the transducers 32 and 34 in order to electrically excite them and to transmit the received information in the form of electrical signals. The pairs of conductors 40 are connected with a pair of electrically conductive strips 42 (see FIG. 3) on the sleeve 24. A pair of slip rings 44 are mounted on the motor shaft 22 and are connected with the respective strips 42 by conductors 46. The slip rings 44 rotate with the motor shaft 22 and are contacted by spring loaded electric contacts 48 which are maintained against the slip rings by compression springs 50 (FIG. 3).

Electrical signals are transmitted to and received from the contacts 48 by a suitable electrical transmitter/receiver 52. The electrical contact that is maintained between the contacts 48 and the slip rings 44 allows the transmission of electrical signals to the transducers 32 and 34 and from the transducers back to the transmitter/receiver 52.

Referring again to FIGS. 4 and 5 in particular, the reflector 38 is mounted on the end of a support tube 53 that fits slidably in the end 28*a* of the probe. The support tube 53 has a projecting tongue 54 which fits in a groove 56 formed in the inside surface of probe 28. The fit of the tongue 54 in the groove 56 provides a track system which allows tube 53 to extend and retract axially in the probe 28.

A rigid actuator wire 58 extends through probe 28 and connects with the support tube 53 at one end. As best shown in FIGS. 3 and 6, the opposite or outer end of the actuator wire 58 extends into a cylinder 60 forming part of a magnetic actuator 62 which adjusts reflector 38 axially within probe 28. The cylinder 60 extends through an electro magnet 64 forming part of the actuator. Mounted slidably within cylinder 60 and connected with the wire 58 is a magnet 66 which is continuously urged to the right as viewed in FIG. 6 or toward the inner end of the catheter assembly by a compression spring 68.

When the electromagnet 64 is deenergized, the spring 68 maintains the magnet 66 in the position shown in broken lines in FIG. 6. Then, the actuator wire 58 pushes the support tube 53 outwardly to position the reflector 38 as shown in FIG. 5 which is the outer most position of the reflector. However, when the electromagnet 64 is energized, the magnetic attraction it exerts on the magnet 66 causes the magnet to retract to the position shown in solid lines in FIG. 6, thus pulling wire 58 and moving the reflector 38 inwardly to the extreme innermost position shown in FIG. 4.

It is thus evident that the electromagnetic actuator 62 is effective to axially adjust the reflector 38 inwardly and outwardly. As the reflector 38 moves inwardly and outwardly, the ultrasonic signal 34*a* reflects from different areas on the curved reflector 38 and thus follows different paths. For example, in the innermost position of the reflector shown in FIG. 4, the reflected signal 34*b* is reflected across the longitudinal axis of probe 28, while in the outermost position of the reflector shown in FIG. 5, the reflected ultrasonic signal 34*b* is directed away from the longitudinal axis of the probe. The reflected signal 34*b* forms an acute angle with the longitudinal axis of the probe at all positions of the reflector 38.

With continued reference to FIGS. 4 and 5, the laser beam that is emitted from the tip of the optical fiber 30 is directed toward an inclined mirror 70. The reflector 70 may be oriented to reflect the laser beam onto the curved mirror 38, or it may be oriented to otherwise direct the laser beam out through the tip end of the probe 28.

FIGS. 8 and 9 depict an alternative arrangement for axially adjusting the reflector 38. In this arrangement, the mirror 38 is carried on the end of an elongated tube 72 which extends through the probe 28 and rotates with the probe by means of a tongue and groove fit or the like. A bearing 74 is fitted on the outer end of tube 72. The outer race of the bearing 74 has a pair of spaced apart flanges 76 between which a cam 78 closely fits. The cam 78 is mounted eccentrically on the output shaft 80 of an electric motor 82. When the motor 82 is operated, the cam 78 is rotated eccentrically, and its action against the flanges 76 causes the tube 72 to reciprocate inwardly and outwardly by camming action. The bearing 74 allows the tube 72 to rotate when the probe 28 is rotated.

FIGS. 10 and 11 depict a mechanism by which the probe 28 may be reciprocated axially relative to the catheter tube 12. An electric motor 84 drives a threaded output shaft 86 which is threaded through the base of a Y-shaped yoke 88. As best shown in FIG. 11, the two arms of the yoke 88 carry rollers 90 which fit closely between a pair of flanges 92 projecting from a spool 94. The spool 94 is secured to a tube 96 that connects with the probe 28.

When the motor is operated in opposite directions, the shaft 68 is rotated in opposite directions to move yoke 88 in opposite directions, thus extending and retracting the probe 28 relative to the catheter tube 12. When the probe is rotated, the tube 96 and spool 94 are rotated with it, and such rotation is permitted by the fit of the rollers 90 between the flanges 92 of the spool.

In operation of the catheter 10, the catheter tube 12 may be inserted into the artery 14 until the catheter tube end 12*a* is adjacent to the area of the plaque 16. the probe 28 may be rotated within the catheter tube, and rotation of the probe sweeps the first transducer 32 around so that the signals 32*a* are swept completely around the circumference of the artery 14. At the same time, the ultrasonic signals 34*b* which emanate from the other transducer 34 are swept in a circular path in order to provide information as to the character and configuration of the plaque 16 located ahead of the probe. The reflector 38 can also be extended and retracted in order to direct the signals 34*b* in different directions to provide an accurate profile of the entirety of the plaque formation. This information is then used to control the laser such that the laser beam emitted from the optical fiber 30 is directed appropriately to destroy the plaque 16 while avoiding damage to the artery walls or other healthy tissue. The probe 28 can be axially extended and retracted by operation of the motor 84 if desired.

The ultrasonic transducers 32 and 34 are operated in a pulse-echo mode and are controlled by a computer which controls other functions as well. The information provided by transducer 32 determines the thickness of the plaque deposit inwardly from the artery wall and also measures the artery wall thickness to make certain that the laser is not directed toward an undamaged artery wall surface. The two ultrasonic transducers are electrically isolated from one another, and it is possible to use either a single pulse generator to alternately excite the two transducers, or a separate pulse generator for each transducer. The pulse generators may produce spike impulses or square waves of appropriate amplitude and duration to drive each of the transducers at its nominal operating frequency.

A graphic display of the outputs from the transducers may be provided. The display for transducer 34 can include the echo amplitude and time of flight information, and these may be incorporated into a graphic representation of the probe in the artery to show the distance ahead of the probe at which the plaque deposit is detected. The display for transducer 32 will similarly include echo amplitude and time of flight information, and this information may be incorporated into a graphic representation of the distance from the probe center line to the interior artery wall as well as the artery wall thickness. The longitudinal and angular positions of the probe may be encoded and used to provide location data that is stored simultaneously with the ultrasonic data. When a probe position is repeated during the course of a particular procedure, the most recent data should overwrite the previous data in order to show how the procedure has changed the condition of the artery. The data may be transferred to memory storage at any time so that before and after comparisons can be later made.

FIG. 12 depicts an alternative arrangement of the components within the tip end of the probe 28. In this arrangement, the second transducer 34 is eliminated and the first transducer 32 is arranged in the manner indicated previously. The optical fiber 30 is offset from the longitudinal axis of the probe and is oriented to direct the laser beam toward an inclined mirror 98. The mirror should reflect the laser beam outwardly in a radial direction as indicated by the beam 100 in FIG. 12. A window 102 is provided in the wall of the probe 28 for passage of the laser beam radially through the tip end of the probe.

The catheter depicted in FIG. 12 operates in substantially the manner previously described, except that the ultrasonic signals are directed radially at all times, and the laser beam 100 is likewise directed radially for the treatment of plaque or other abnormalities.

FIG. 12a illustrates still another arrangement of components in the tip end of the probe 28. A reflector 103 is mounted in the tip end of the probe and includes two sections arranged at a right angle to one another and at 45° to the longitudinal axis of the catheter. The two transducers 32 and 34 emit ultrasound toward the two sections of reflector 103. Transducer 32 emits ultrasound toward one section of the reflector in a direction to reflect through window 36 in a radial pattern, as indicated at 32a. The other transducer 34 emits ultrasound toward the other section of reflector 103 in a direction to reflect forwardly parallel to the longitudinal axis of the catheter, as indicated at 34a.

In the embodiment of FIG. 12a, there are two optical fibers 30 for transmitting laser energy. One fiber 30 is arranged to emit a laser beam which reflects from one section of reflector 103 and through window 102 in a radial direction, as indicated at 100. The other fiber 30 extends through the reflector 103 and directs its laser beam forwardly along the catheter axis.

FIGS. 13 and 14 depict another alternative arrangement of the catheter 10. In this embodiment of the invention, the probe 28 is stationary relative to the catheter tube 12. A plurality of the optical fibers 30 extend through the catheter 12 and are arranged around the circumference of the probe 28 in a circular pattern (see FIG. 14). The tip end of the probe 28 is provided with a conical mirror 104 which is located to receive the laser beams emitted by the fibers 30 and to reflect the beams radially outwardly. Because the fibers are arranged around the entire circumference of the probe, substantially the entirety of the artery wall circumference can be treated by the fibers. Control of which of the fibers 30 is to receive laser energy may be effected by a suitable switching system under computer control.

Mounted on the free end of the mirror 104 is an ultrasonic head 106 provided with a phased array of ultrasonic transducers 108 arranged to direct ultrasonic signals radially outwardly around substantially the entire circumference of the probe 28. The electrical conductors 40 extend to the phased array of ultrasonic transducers.

The catheter shown in FIGS. 13 and 14 uses the phased array of ultrasonic transducers 108 to provide information as to the configuration and thickness of the plaque deposits located radially outwardly from the tip of the probe. The fibers 30 are energized in the desired pattern with laser energy in order to destroy the plaque deposit while avoiding damage to the artery walls.

FIG. 15 depicts still another alternative arrangement for the tip portion of the probe 28. In this embodiment of the invention, an ultrasonic transducer 110 is carried on the extreme tip of the probe 28 and is oriented relative to the longitudinal axis of the probe at an angle in the range of 4–10 degrees. The transducer 110 emits ultrasonic signals in a conical pattern, with the cone angle determined by the frequency of the electrical signals used to excite the transducer. For example, when the signals are at a relatively high excitation frequency of 20 mhz, the cone configuration is indicated by numeral 112 and has a very tight cone angle that approaches the shape of a cylinder. As the frequencies decrease to 5 mhz, the cone angle increases as indicated by the conical shape 114. Decreasing the excitation frequency to 3 mhz generates the cone pattern 116, and the cone angle is greater yet. In all cases, the major access of the cone makes an acute angle relative to the longitudinal axis of the probe.

A plurality of the optical fibers 30 extend to the tip of the probe and are energized in a selected pattern to treat the occlusion which is sensed by the ultrasonic transducer 110.

FIG. 16 depicts in block diagram form a system which may be used to excite the transducer 110. A variable frequency oscillator 118 is used in combination with a gated amplifier 120. A pulse width generator 122 controlled by a trigger circuit 124 operates a gate selector 126 which in turn controls the amplifier 120. The output from the amplifier provides a series of radio frequency pulses that are applied to the transducer 110.

The transducer 110 should have a broad band width which is typically 2.5–4 times the nominal center frequency. It may be a single element transducer. Alternatively, a wider frequency range can be covered by using two transducer elements, one having a nominal center frequency that is 2–3 times that of the other. The impulse generator which excites the transducer is frequency tunable, as previously indicated. It may be a tone burst device that produces a selected number of sinusoidal impulses that have a selected time duration, amplitude and number of impulses. The tone burst may be produced by the gated amplifier 120 or by a pulsed oscillator. The excitation device may also be a single or multiple square wave generator of selected amplitude, duration and number of square waves in a single burst.

By selectively controlling the impulse characteristics, the transducer is selectively operated at various narrow band frequencies that are within its overall frequency range. For each operating frequency that is used, there is a characteristic beam pattern which defines the volume within the artery from which ultrasonic reflections may be detected, as exemplified by the cone shapes depicted in FIG. 15 as the cones 112, 114 and 116.

The transducer 110 is operated in the pulse echo mode. Returning echoes are characterized by amplitude, time of flight and frequency. This information defines a sector of the artery within which the reflective tissue is located. Lower frequency operation produces a broader ultrasonic beam for impingement on a normal artery wall to produce reflections from relatively thin deposits. Increasing the operating frequency produces a narrower beam that produces reflections only from deposits that protrude farther inwardly from the artery wall. Thus, the highest frequency at which a reflection is received from a particular deposit indicates the thickness of the deposit or the extent of the artery blockage.

A potentially ambiguous response, such as a response from a deposit on the outside curvature at a bend in an artery, can be resolved by rotating the probe while sweeping through the frequency range of the transducer. The longitudinal and angular positions of the probe are controlled by encoded mechanical devices. The encoders are used to provide location data simultaneously with the ultrasonic data.

The ultrasonic signals should be processed by a receiver/amplifier which may be broad banded in order to cover the entire operating frequency and width. It can incorporate a series of high pass filters that are switched in and out as the transducer excitation frequency is switched. Alternatively, a series of narrow to medium band width filters can be used and switched in sequence with a series of discrete excitation frequencies.

Alternatively, the transducer 110 may be constructed to have a very narrow band width. The transducer can be excited at its nominal natural frequency or at some multiple thereof. This provides a more powerful ultrasonic output than a broad band transducer, and it may be more suitable for relatively large arteries. However, because a more powerful output produces a longer decay time for the initial pulse, a narrow band width system is relatively insensitive to reflectors that are very close to the probe tip. This problem can be overcome by providing the ultrasonic device with separate transmitting and receiving elements which are electrically isolated from one another so that the receiving element does not receive the initial excitation impulse. The receiving element is thus able to respond to reflection that would otherwise be impossible to distinguish from aberrations in the excitation pulse.

It should be noted that with either a broad band width or narrow band width system, an acoustic lens can be added to the face of the transducer to either increase or decrease the amount of beam spread at a given operating frequency and/or to alter the angle of the central ray of the beam with respect to the axis of the artery.

FIGS. 17 and 18 depict still another embodiment of the catheter. In this arrangement, the transducer 32 is oriented to direct its ultrasonic signal 32a toward an inclined mirror 128 which reflects the signal in a radial direction through a window 130 in the wall of the probe 28. The reflected signal 32b is directed radially outwardly.

The other transducer 34 is oriented to direct its ultrasonic signal 34a toward another inclined mirror 132. The reflected signal 34b is oriented parallel to the longitudinal axis of the probe 28.

Transducer 32 thus transmits signals that are oriented radially to determine the thickness of the plaque along the artery wall during rotation of the probe. The other transducer 34 generates a signal forwardly of the probe to provide information as to the plaque deposit ahead of the probe.

The optical fiber 30 may extend through mirror 132 in order to direct the laser beam generally forwardly at a location offset from the longitudinal axis of the probe.

Still another alternative embodiment of the catheter is depicted in FIGS. 19–23. Referring first to FIG. 19, a plurality of optical fibers 30 extend from a shutter mechanism 134 and through the probe 28. As shown additionally in FIG. 22, the fibers 30 occupy only approximately ½ the diameter of the probe 28, with a tube 136 located in the remaining ½. The fibers 30 are arranged uniquely such that the fibers whose inner ends 30a are closest to the longitudinal axis of the probe, have their outer ends 30b located farthest from the center of the probe. Conversely, the fibers whose inner ends 30a are located farthest from the center of the probe have their outer ends 30b located closest to the center.

As shown in FIGS. 20 and 21, the shutter 134 has a plurality of pivotal shutter elements 138. When the shutter elements 138 are pivoted fully outwardly, the shutter is fully open, and the ends 30b of all of the fibers 30 are exposed through the shutter. When the elements are pivoted inwardly from the fully opened position, the shutter progressively closes and the shutter opening 140 becomes smaller such that the ends 30b of only some of the fibers are exposed through the shutter opening. The laser energy is transmitted through the shutter opening and is applied to those fibers whose ends 30b are exposed.

It is noted that as a shutter progressively closes, the fiber ends 30b farthest from the center of the probe are progressively covered by the shutter, and the corresponding fibers have their inner ends 38 closest to the center of the probe. Consequently, as the shutter closes, the laser energy is progressively transmitted only through those fibers whose inner ends 30a are located closest to the perimeter of the probe 28. As a result, as the shutter is closed, the area within the artery closest to the artery wall is treated last.

The tube 136 is provided with an ultrasonic transducer 142 which is excited through electrical wiring 144 extending in the tube. The ultrasonic signal 142a emitted by transducer 142 is intercepted by an inclined mirror 146 and reflected by the mirror in a forward direction parallel to the longitudinal axis of the probe, as indicated in FIG. 23 by numeral 142b.

The probe 28 is rotatable in the catheter tube 12, and the tube 136 is rotatable within the probe. Consequently, by rotating the probe and the tube 136, the ultrasonic signals can sense the profile of the entirety of the artery. Also, the fibers 30 can be directed at the plaque deposits as the probe rotates.

FIGS. 24 and 25 depict yet another embodiment of the catheter 10. In this arrangement, a plurality of optical fibers 30 extend through an elongated tube 148 which in turn extends through the probe 28 and is centered on its longitudinal axis. An ultrasonic transducer (not shown) similar to those described previously is carried on the inner end of an elongated tube 150 which extends through the probe parallel to tube 148 but is considerably smaller.

The tubes 148 and 150 extend through a stationary cylinder 152. At one end of the cylinder 152, a bar 154 extends diametrically across the cylinder and is fixed to the end of tube 148. A drive roller 156 fixed to tube 150 is mounted for rotation on one end of bar 154 and rolls against the inside surface of cylinder 152. On the opposite end of bar 154, an idler roller 158 is mounted for rotation and rolls against the inside surface of cylinder 152.

The bar 154 can be rotated by any suitable mechanism such as an electric motor (not shown). As bar 154 is rotated, tube 148 is rotated with it to rotate the optical fibers 30. At the same time, the rolling movement of roller 156 against the inside surface of cylinder 152 causes roller 156 to rotate faster than tube 148 and in an opposite direction, as indicated by the directional arrows in FIG. 25. Consequently, when bar 154 is rotated, tube 148 is rotated in one direction and tube 150 is rotated in the opposite direction and at a faster rate. Rotation of tube 150 carries the ultrasonic transducer in the pattern depicted in FIG. 26 so that the transducer is able to direct ultrasonic signals in a manner to sense the configuration of the entirety of the inside of the artery.

Although the various embodiments of the invention have been described in connection with the treatment of arterial plaque, it is understood that the catheter can be used in the laser treatment of other medical conditions. For example, tumors and other abnormalities can be treated with laser energy in the colon, prostate, esophagus and other organs and internal body parts. It should also be understood that the various ultrasound systems can be used alone as forward looking ultrasound schemes for detecting the configurations in arteries and other internal body parts, as well as in combinations with other interactive treatment means such as atherectomy. As one example, the catheter shown in FIG. 23 cap be used with an atherectomy device replacing the optical fibers and with the ultrasound system used to help direct the direction and control of the atherectomy device.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, we claim:

1. In a catheter for insertion into areas of the body such as arteries, an ultrasonic system comprising:
    an elongated catheter tube having opposite ends and defining a longitudinal axis, said catheter tube being flexible to accommodate insertion into arteries and other areas of the body;
    an elongated flexible probe extending through said catheter tube and axially rotatable therein;
    a motor for rotating said probe;
    at least one ultrasonic transducer carried on said probe adjacent one end thereof for transmitting and receiving ultrasonic signals, and said transducer rotating with said probe and being arranged to direct transmitted ultrasonic signals along a prescribed path;
    a reflector carried on said probe at a location along said prescribed path to reflect said ultrasonic signals at an angle;
    an elongate actuator wire having inner and outer ends, said wire inner end coupled to said probe;
    an actuator coupled to said actuator wire outer end for adjusting said reflector linearly in a direction substantially parallel to said longitudinal axis of said catheter tube to thereby vary, relative to said longitudinal axis of said catheter tube, said angle relative to said longitudinal axis at which said signals are reflected by said reflector;
    a conductive strip extending through said probe to said ultrasonic transducer for conducting electrical signals thereto;
    at least two slip rings located exteriorly of the catheter; and
    at least two contact movably coupled to said slip rings for applying said electrical signals to said conductive strip for excitation of said ultrasonic transducer while said probe is rotating.

2. A catheter in accordance with claim 1 wherein said catheter is coupled to a laser, said catheter further comprising at least one optical fiber to provide a path for transmitting and receiving energy from the laser to the artery.

3. A catheter in accordance with claim 1 wherein said probe comprises at least one window, and wherein said ultrasonic signals are transmitted and received through said window.

4. A catheter in accordance with claim 1 further comprising a second ultrasonic transducer carried on said probe adjacent to one end thereof for transmitting and receiving ultrasonic signals, and said second ultrasonic transducer rotating with said probe and being arranged to direct transmitted ultrasonic signals in a direction radial to said longitudinal axis.

5. A catheter in accordance with claim 1 wherein said actuator for adjusting said reflector comprises a magnetic actuator.

6. In a catheter for insertion into areas of the body such as arteries, an ultrasound system comprising:
    an elongated catheter tube having opposite ends and defining a longitudinal axis, said catheter tube being flexible to accommodate insertion into arteries and other areas of the body;
    an elongated flexible probe extending through said catheter tube and axially rotatable therein;
    power means for rotating said probe;
    a first ultrasonic transducer carried on said probe adjacent one end thereof for transmitting and receiving ultrasonic signals, and first transducer rotating with said probe and being arranged to direct transmitted ultrasonic signals in a direction radial to said longitudinal axis;
    a second ultrasonic transducer carried on said probe adjacent said one end thereof for transmitting and receiving ultrasonic signals, said second transducer rotating with said probe and being arranged to direct transmitted ultrasonic signals along a prescribed path;
    a reflector carried on said probe at a location along said prescribed path to reflect the ultrasonic signals transmitted by said second transducer, said reflector being curved and reflecting said ultrasonic signals at an angle;
    means for adjusting said reflector linearly in a direction substantially parallel to the longitudinal axis of the catheter tube to thereby vary, relative to the longitudinal dimension of the catheter tube, the angle relative to the longitudinal axis at which the signals are reflected by said reflector;
    electrical conductor means extending through the probe to said first and second transducers for conducting electrical signals thereto; and
    means located exteriorly of the catheter tube for applying electrical signals to said conductor means for excitation of said first and second transducers while said probe is rotating.

7. A catheter in accordance with claim 6 wherein said prescribed path is substantially perpendicular to said longitudinal axis of said catheter tube.

8. A catheter in accordance with claim 6 wherein said transducers are piezoelectric ceramic crystals.

9. A catheter in accordance with claim 6 wherein said reflector reflects said second transducer ultrasonic signals at an acute angle relative to said tube longitudinal axis.

10. A catheter in accordance with claim 6 wherein said power means for rotating said probe is an electrical stepping motor.

11. A catheter in accordance with claim 6 wherein said probe comprises at least one window, and wherein said ultrasonic signals are transmitted and received through said window.

12. A catheter in accordance with claim 6 wherein said electrical conductor means is a conductive strip.

13. A catheter in accordance with claim 6 wherein said means for adjusting said reflector comprises:

an elongate actuator wire extending through said probe to said reflector for axially reciprocating said reflector when said wire is extended and retracted; and means for extending and retracting said actuator wire.

14. A catheter in accordance with claim 6 wherein said means for extending and retracting said actuator wire comprises a magnetic actuator.

15. A catheter in accordance with claim 6 wherein said catheter tube further comprises an annular balloon seal adapted to provide a seal against an artery.

16. A catheter in accordance with claim 6 wherein said probe comprises at least one optical fiber to provide a path for transmitting and receiving energy from a laser.

17. A catheter in accordance with claim 6 wherein said reflector is an axially translatable mirror.

18. In a catheter for insertion into areas of the body such as arteries, an ultrasonic system comprising:

an elongated catheter tube having opposite ends and defining a longitudinal axis, said catheter tube being flexible to accommodate insertion into arteries and other areas of the body;

an elongated flexible probe extending through said catheter tube and axially rotatable therein;

a motor for rotating said probe;

a first ultrasonic transducer carried on said probe adjacent one end thereof for transmitting and receiving ultrasonic signals, and first transducer rotating with said probe and being arranged to direct transmitted ultrasonic signals in a direction radial to said longitudinal axis;

a second ultrasonic transducer carried on said probe adjacent one end thereof for transmitting and receiving ultrasonic signals, said second transducer rotating with said probe and being arranged to direct transmitted ultrasonic signals along a prescribed path;

a reflector carried on said probe at a location along said prescribed path to reflect said ultrasonic signals transmitted by said second transducer, said reflector being curved and reflecting said ultrasonic signals at an angle;

an actuator wire having inner and outer ends, said inner end coupled to said probe;

an actuator coupled to said actuator wire outer end for extending and retracting said probe, wherein extending and retracting said probe moves said reflector linearly in a direction substantially parallel to said longitudinal axis of said catheter tube to thereby vary, relative to said longitudinal axis of said catheter tube, said angle relative to said longitudinal axis at which said signals are reflected by said reflector;

at least two conductive strips extending through said probe, said strips coupled to said first and second ultrasonic transducers for conducting electrical signals thereto;

at least two slip rings coupled to an outer diameter of said catheter tube; and at least two contacts rotatably coupled to said slip rings for applying said electrical signals to said conductive strips for excitation of said first and second ultrasonic transducers while said probe is rotating.

* * * * *